United States Patent [19]

Ellgen et al.

[11] 4,014,913

[45] Mar. 29, 1977

[54] PROCESS FOR PRODUCING OXYGENATED TWO CARBON COMPOUNDS

[75] Inventors: Paul Clifford Ellgen, St. Albans; Madan Mohan Bhasin, Charleston, both of W. Va.

[73] Assignee: Union Carbide Corporation, New York, N.Y.

[22] Filed: June 26, 1975

[21] Appl. No.: 590,717

[52] U.S. Cl. .......................................... 260/449 R
[51] Int. Cl.$^2$ ....................................... C07C 27/06
[58] Field of Search ............................... 260/449 R

[56] References Cited

UNITED STATES PATENTS 1,984,884   12/1934   Lazier ........................... 260/449 R
3,833,634   9/1974   Pruett et al. ................... 260/449 R

*Primary Examiner*—Howard T. Mars
*Attorney, Agent, or Firm*—Bernard Lieberman

[57] ABSTRACT

A process for the selective preparation of two-carbon atom oxygenated hydrocarbons, namely acetic acid, ethanol, and acetaldehyde, by continuously contacting a reaction mixture containing hydrogen and carbon monoxide with a rhodium-manganese catalyst, at a combination of reaction conditions correlated so as to favor the formation of a substantial proportion of these products.

5 Claims, No Drawings

PROCESS FOR PRODUCING OXYGENATED TWO CARBON COMPOUNDS

CROSS-REFERENCE TO RELATED APPLICATIONS

This application is related to copending U.S. applications Ser. No. 437,141, filed Jan. 28, 1974, and now abandoned; U.S. application Ser. No. 541,661, filed Jan. 16, 1975, and now abandoned and U.S. application Ser. No. 541,660 filed Jan. 16, 1975, and now abandoned, and describes an improvement in the processes described in those applications.

BACKGROUND

This invention concerns an improvement in the selective preparation of two-carbon atom oxygenated hydrocarbons, namely acetic acid, ethanol, and/or acetaldehyde, from synthesis gas. More particularly, the invention concerns reaction of synthesis gas in the presence of a rhodium-manganese catalyst under heterogeneous reaction conditions to produce such products.

The preparation of hydrocarbons and oxygenated hydrocarbons from synthesis gas (essentially a mixture of carbon monoxide with varying amounts of carbon dioxide and hydrogen) has received extensive study and has achieved commercial adoption. Reaction conditions generally involve temperatures on the order of 150°–450° C, pressures from atmospheric to about 10,000 psig, and hydrogen-to-carbon monoxide ratios in the range of 4:1 to about 1:4, with an iron group or a noble metal group hydrogenation catalyst.

One serious disability of most synthesis gas processes has been the non-selective or non-specific nature of the product distribution. Catalysts which possess acceptable activity generally tend to give a wide spectrum of products, for example, hydrocarbons and oxygenated hydrocarbons having a broad distribution of carbon atom contents. This not only complicates the recovery of desired products, but results in the wastage of reactants to commercially uninteresting byproducts.

In copending application Ser. No. 541,661 and in its parent Ser. No. 437,141, there have been described a process for the selective preparation of two-carbon atom oxygenated hydrocarbons, namely acetic acid, ethanol, and acetaldehyde, using a rhodium catalyst.

SUMMARY OF INVENTION

Rhodium, however, is expensive and its availability is limited. It has now been discovered that it is possible to reduce the quantity of rhodium necessary to attain a desired catalyst activity or increase the activity with a given quantity of rhodium, while retaining the selectivity toward two-carbon atom oxygenated compounds as described in the aforesaid copending applications.

Briefly, in accordance with the invention, a continuous process is provided for the reaction of a synthesis gas containing carbon monoxide and hydrogen to prepare two carbon atom oxygenated hydrocarbons by continuously contacting the gas with a catalyst comprising rhodium and manganese, under suitable reaction conditions.

PROCESS DISCUSSION

The reaction is conducted at reaction conditions of temperature, pressure, gas composition and space velocity correlated so as to collectively produce acetic acid, ethanol, and/or acetaldehyde in an amount which is at least about 50 weight percent, preferably at least about 75 weight percent, of the two and more carbon atom compounds obtained by the reaction. Desirably, the reaction is conducted at these correlated conditions to achieve product efficiencies based on carbon consumption in excess of 10%, and frequently in excess of 50%. Ethyl esters and acetates formed are included as ethanol and acetic acid in determining productivities and selectivities as used in data presented herein. At optimum reaction conditions, and particularly at relatively low conversions, there is little conversion to three carbon atom and higher hydrocarbons and oxygenated hydrocarbons, and conversion to methane and methanol may readily be minimized. The reaction efficiency, or selectivity, to these two-carbon atom compounds is invariably at least about 10%, and is usually upwards of about 25%; under the preferred conditions it exceeds 50% and, under optimum conditions, can reach 90% or more. Selectivity is defined herein as the percentage of carbon atoms converted from carbon monoxide to a specified compound or compounds other than $CO_2$.

Thus, the independent reaction variables are correlated so as to favor the formation of a substantial proportion of the desired two carbon atom oxygenated hydrocarbons (acetic acid, ethanol, and/or acetaldehyde). This proportion, expressed as carbon conversion efficiency, is usually upwards of 25% and frequently exceeds 50%.

In one aspect of the invention, this correlation is a combination of conditions which result in maintaining moderate reaction conditions to thereby limit the conversion of CO to not more than about one fourth, preferably not more than about one eighth. As will be discussed in detail below, this may be achieved primarily by a combination of high space velocity and low temperature, but other factors (e.g. $H_2/CO$ ratio, catalyst activity, pressure, bed geometry, etc.) also affect the conversion. At high conversions, it has been noted that hydrocarbons and higher carbon number oxygenated hydrocarbons are produced in excess, with a resulting loss in efficiency to two-carbon atom compounds.

Conditions of temperature, of pressure, and of gas composition are usually within the ranges that are essentially conventional for synthesis gas conversions, particularly those employed in the production of methanol. Thus, existing technology and, in some instances, existing equipment may be used to effect the reaction.

The reaction is highly exothermic, with both the thermodynamic equilibrium and the kinetic reaction rates being governed by the reaction temperature. Average catalyst bed temperatures are usually within the range of about 150°–450° C., but for optimum conversions, bed temperatures are kept within the range of about 200°–400° C., typically about 250°–350° C.

The reaction temperature is an important process variable, affecting not only total productivity but selectivity toward one or more of the desired two carbon atom products. Over relatively narrow temperature ranges, as for example 10° or 20° C., an increase in temperature may somewhat increase total synthesis gas conversion, tending to increase the efficiency of ethanol production and decrease the efficiency of acetic acid and acetaldehyde production. At the same time, however, higher temperatures favor methane production, and apparently methane production increases much more rapidly at higher temperatures than do conversions to the more desirable two carbon atom products. Thus, for a given catalyst and with all other variables held constant, the optimum temperature will depend more on product and process economics than on thermodynamic or kinetic considerations, with higher temperatures tending to increase the production of oxygenated products but disproportionately increasing the co-production of methane.

In the discussions above the indicated temperatures are expressed as average, or mean, reaction bed temperatures. Because of the highly exothermic nature of the reaction, it is desirable that the temperature be controlled so as not to produce a runaway methanation, in which methane formation is increased with higher temperature, and the resulting exotherm increases the temperature further. To accomplish this, conventional temperature control techniques are utilized, as for example the use of fluidized bed reaction zones, the use of multi-stage fixed bed adiabatic reactors with interstage cooling, or relatively small catalyst particles placed in tube-and-shell type reactors with a coolant fluid surrounding the catalyst-filled tubes. In this regard, reference is made to U.S. application Ser. No. 590,718, filed on even date herewith.

The reaction zone pressure is desirably within the range of about 15 psig to about 10,000 psig, economically within the range of about 300–5,000 psig. Higher reaction zone pressures increase the total weight of product obtained per unit time and likewise improve the selectivity toward two carbon atom compounds.

The ratio of hydrogen to carbon monoxide in the synthesis gas may vary widely. Normally the mole ratio of hydrogen to carbon monoxide is within the range of 20:1 to 1:20, or preferably within the range of about 5:1 to about 1:5. In most of the experimental work reported herein the mole ratio of the hydrogen to carbon monoxide is somewhat less than 1:1. Increasing the ratio tends to increase the total rate of reaction, sometimes quite significantly, and has a small though favorable effect on production of two carbon atom products, but concurrently increases selectivity to methane. Increasing the hydrogen to carbon monoxide ratio also favors the formation of more highly reduced products, that is, ethanol rather than acetaldehyde or acetic acid.

Carbon dioxide, normally present in an amount of up to about 10 mole percent, in the synthesis gas has essentially no effect. If a recycle operation is conducted, in which all or part of the reacted gas is recycled to the catalyst zone, it is desirable to remove oxygenated hydrocarbons before recycling.

One of the features of the present invention is the recognition that a low conversion, e.g., preferably less than 20% of the CO, favors the formation or production of a substantial proportion of acetic acid, ethanol and/or acetaldehyde, generally in excess of 10%. This conversion is conveniently achieved by employing a high space velocity correlated with other reaction variables (e.g. temperature, pressure, gas composition, catalyst, etc.). Space velocities in excess of about $10^3$ gas hourly space velocity (volumes of reactant gas, at 0° C and 760mm mercury pressure, per volume of catalyst per hour) are generally employed, although it is preferable that the space velocity be within the range of about $10^4$ to about $10^6$ per hour. Excessively high space velocities result in uneconomically low conversions, while excessively low space velocities cause the production of a more diverse spectrum of reaction products, including higher boiling hydrocarbons and oxygenated hydrocarbons.

The rhodium-manganese catalyst is rhodium provided in combination with manganese upon a support material. This is typically effected by depositing rhodium and manganese onto a particulate support material and placing the supported rhodium-manganese combination into the reaction zone.

On the basis of experience to date the amount of catalysts on the support should range from about 0.01 weight percent to about 25 weight percent, based on the combined weight of the metal catalyst and the support material. Preferably, the amount of catalyst is within the range of about 0.1 to about 10 weight percent.

A wide variety of support materials has been tested. A relatively high surface area particulate support, e.g. one having a surface area upwards of about 1.0 square meters per gram (BET low temperature nitrogen adsorption isotherm method), is preferred, desirably upwards of about 10 square meters per gram, although surface area alone is not the sole determinative variable. Based on research to date, silica gel is preferred as the catalyst base or support, with graphite, graphitized carbon, alpha alumina, manganese oxides, magnesia, etaalumina, gamma-alumina, and active carbon being progressively less desirable. Zeolitic molecular sieves, primarily the higher silica-to-alumina crystalline zeolites, also have promise.

For the purposes of this invention, it is believed that rhodium deposited on particles of manganese oxides is the same or not significantly different from rhodium and manganese codeposited on any of the above support materials, including manganese oxides.

The rhodium and the manganese may be deposited onto the base or support by any of the techniques commonly used for catalyst preparation, as for example impregnation from an organic or inorganic solution, precipitation, coprecipitation, or cation exchange (on a zeolite). Conveniently, a solution of a heat decomposable inorganic or organic rhodium compound and a manganese compound is appropriately contacted with the support material, and the support then dried and heated, the latter advantageously under reducing conditions, to form the finely dispersed manganese-containing rhodium catalyst. These materials may be deposited concurrently or sequentially. It suffices for the present to say that inorganic or organic rhodium and manganese compounds are appropriately contacted with the support material, and the support then dried and heated, the latter advantageously under reducing conditions, to form the finely dispersed rhodium and manganese.

The rhodium deposited is typically in metal form, desirably as fine discrete particles. The form of the manganese component is, however, not completely appreciated. It may be chemically associated with the rhodium or it may be in a physical admixture with the rhodium. For example, the manganese may be alloyed with the rhodium or not, in the form of a metal or an oxidized state of the metal, or it may be in oxide or a silicate, carbonate, and the like, form.

Description of Test Reactor

The reactor used in these studies was an internally gold-plated bottom-agitated "Magnedrive" autoclave of the J. M. Berty design with a centrally positioned catalyst basket and a side product effluent line. It is of the type depicted in FIG. 1 of the paper by Berty, Hambrick, Malone and Ullock, entitled "Reactor for Vapor-Phase Catalytic Studies", presented as Preprint 42E at the Symposium on Advances in High-Pressure Technology — Part II, Sixty Fourth National Meeting of the American Institute of Chemical Engineers (AIChE), at New Orleans, Louisiana, on March 16–20, 1969 and obtainable from AIChE at 345 East 47 Street, New York, N.Y. 10017. A variable speed, magnetically driven fan continuously recirculated the reaction mixture over the catalyst bed. The following modifications were found to facilitate operation and inhibit run-away methanation reactions.

1. Hydrogen feed gas was introduced continuously at the bottom of the autoclave through the well for the shaft of the Magnedrive agitator.

2. Carbon monoxide feed gas was introduced continuously through a separate port at the bottom of the autoclave, in order to avoid a hydrogen-rich zone in the autoclave. When carbon dioxide was fed, it was added with the carbon monoxide feed stream.

Effluent gases are removed through a port in the side of the reactor. Condensable liquid products are removed from the exit stream in a brine-cooled condenser at ca. 5 to 10° C. and are collected in a holding tank under pressure. The non-condensable components of the exit stream are vented through a wet test meter at atmospheric pressure to determine their total volume. A rubber septum in the atmospheric pressure line permits syringe sampling of the non-condensable gases. No external recycle is employed.

Description of the Test Procedure

The bulk volume of a weighed catalyst sample is determined, and the sample is placed in the catalyst basket. The quantity of catalyst charged varies from about 4 grams to about 60 grams. The quantity of a particular catalyst to be charged is chosen to give an estimated reactant gas conversion of less time than 10 percent. Gold-plated screens and thin layers of glass wool are placed above and below the catalyst bed to prevent circulation of solid fines. The catalyst basket is charged to the reactor, and the reactor is sealed. The sealed reactor and the process lines are pressure tested at ambient temperatures to a pressure about 500 to 1000 psig in excess of the maximum anticipated working pressure. Nitrogen, hydrogen, or a mixture of the two is used for this test.

When the reactor is shown to be leak free, pure hydrogen is passed through the reactor, and the temperature is raised to about 240° C. The hydrogen and carbon monoxide flows are then adjusted to give the desired steady-state ratio at the desired approximate purge rate. The purge rate is typically from about 250 STP* liters/hr to about 800 STP* liters/hr. The hydrogen-carbon monoxide ratio is determined by gas chromatographic analysis of an effluent gas aliquot. "STP" means standard temperature pressure defined as 0° C at 1 atm. pressure.

When the appropriate gas composition is obtained, the reactor temperature is raised to the value desired. A period from about 0.5 hour to about one hour is allowed for the reactor to reach a steady state at the new temperature. The liquid product trap is then drained, a wet test meter reading is taken, and the time is noted as the beginning of a run. During the course of a run, one or more effluent gas samples are analyzed for hydrogen, carbon monoxide, acetaldehyde, methane, and other volatile hydrocarbons. At the end of a run, the liquid product is collected, and the volume of effluent gas is noted. The liquid product is analyzed by gas chromatography.

Succeeding runs with the same catalyst may be made either at the same conditions or at new conditions of temperature or feed gas flow rates. If any of these conditions are changed, approximately one hour is allowed for the reactor to come to a new steady-state before beginning a new run.

Preparation of Catalysts

Catalysts cited in the table below were all prepared by essentially the following sequence of steps: The desired quantities of rhodium trichloride and/or manganese nitrate were dissolved in distilled water at ambient temperature. The volume of distilled water taken for the preparation of this solution is chosen to just fill the void volume (pores) of the support sample being impregnated. Davison TM Grade 59 silica gel (3–6 mesh-U.S. Sieves) was placed in a vacuum flask. The top of the flask was sealed with a rubber septum, and the flask was evacuated through the side arm. A syringe needle was then used to inject the solution onto the evacuated support. When addition was complete, the impregnated support was allowed to stand at one atmosphere for ca. 30 minutes. It was then carefully dried in a nitrogen atmosphere using the following sequence: 80° C (for 1 hr.); 110° C. (2 hrs.); 150° C. (2 hrs.); 250° C. (2 hrs.). The dried, impregnated support was placed in a quartz tube through which hydrogen was continuously passed. The temperature was raised from 100° to 500° C., over a six hour period and then held at 500° C. for 1 hour. The reduced catalyst was cooled to ambient temperature in an atmosphere of flowing nitrogen or hydrogen.

The table below summarizes the data for a series of silica-gel-supported rhodium, manganese, and rhodium-manganese catalysts, which were tested at 300° C., 1000 psig total pressure, and a hydrogen-to-carbon-monoxide mole ratio of about unity, according to the above test procedure in the aforementioned test reactor.

The table shows that rhodium–manganese catalysts are much more active than rhodium catalysts for the synthesis of acetaldehyde, acetic acid, and ethanol from synthesis gas. The effect is clearly one of manganese acting as a promoter for the rhodium catalyst, because a catalyst prepared in the same way, but which contains only manganese, is much less active under the same synthesis conditions. The product distributions from rhodium and rhodium-manganese catalysts are very similar. The magnitude of the effect due to the presence of manganese in the catalyst is large. If the comparison is made on the basis of pounds of two-carbon oxygenated products produced per cubic foot of catalyst per hour, the manganese-containing catalysts shown in the table are as much as about seven times as active as catalysts containing the same proportion of rhodium and no manganese. If the comparison is made on the basis of pounds of two-carbon oxygenated products produced per gram of exposed rhodium per hour (specific activity), the manganese-containing catalysts are as much as seventeen times as active.

The table also shows that when a series of catalysts containing a constant proportion of manganese but a decreasing proportion of rhodium is examined, the catalyst activity is seen to decrease disproportionately as the rhodium content decreases. That is, the specific activity of the catalysts, which would normally be expected to remain constant, decreases as the rhodium content decreases in the series.

However, when a series of catalysts containing a constant proportion of rhodium but an increasing proportion of manganese is examined, the catalyst activity is seen to increase. The magnitude of the activity increase observed for a given incremental increase in the manganese content decreases as the manganese content increases. The maximum amount of manganese one could employ under these conditions has not been established but it seems safe to conclude that a large amount could be effectively employed.

The mole ratio of manganese to rhodium in the catalyst in order to gain some advantage should not be less than 1:1000 (i.e., 0.001).

correlated to achieve such product in efficiencies, based on carbon consumption, in excess of 10% and obtain the formation of acetic acid, ethanol, and/or acetaldehyde in an amount which is at least about 50 weight percent of the two or more carbon atom compounds obtained by the reaction, which reaction conditions include a temperature within the range of about 150°–450° C, and a pressure within the range of about 15–10,000 psig and wherein the mole ratio of manganese to rhodium in the catalyst is not less than 1:1000.

2. Process of claim 1 wherein said reaction conditions include a mole ratio of hydrogen to carbon monoxide within the range of about 20:1 to 1:20.

3. Process of claim 2 wherein said reactive conditions include a temperature within the range of about

TABLE

COMPARISON[a] OF SILICA-GEL-SUPPORTED RHODIUM-MANGANESE CATALYSTS

| Catalyst | | Dispersion[b] % | Carbon Efficiency[c] | | | | Rate to $C_2$ Products | |
|---|---|---|---|---|---|---|---|---|
| % RH | % Mn | | Hydrocarbon | Acetaldehyde | Ethanol[d] | Acetic Acid[d] | (lb/of/hr)[e] | (lb/gm Surf Rh/hr)[f] |
| 0. | 3.0 | — | 81. | .7 | 13. | 2. | .06 | — |
| 2.5 | 0. | 31.7 | 37. | 13. | 16. | 28. | 2.5 | .028 |
| 2.5 | 0. | 31.7 | 30. | 25. | 21. | 24. | 3.5 | .039 |
| 1.1 | 3.0 | 11.0 | 59. | 12. | 10. | 17. | 4.0 | .29 |
| 1.56 | .31 | 28.3 | 20. | 24. | 11. | 40. | 15. | .30 |
| 5.0 | .80 | 18.3 | 50. | 21. | 3.0 | 23. | 27. | .26 |
| 2.5 | 1.33 | 17.0 | 65. | 14. | 4.6 | 14. | 12. | .24 |
| 2.5 | .80[h] | 17.4 | 31. | 31. | 6.8 | 26. | 19. | .39 |
| 2.5 | .40 | 22.4 | 39. | 29. | 5.0 | 22. | 23. | .39 |
| 2.5 | .27 | 27.4 | 30. | 24. | 11. | 30. | 16. | .22 |
| 2.5 | .05 | 22.9 | 35. | 18. | 16. | 26. | 5.6 | .088 |
| 2.5 | 5.0 | 12.2 | 58. | 15. | 5.7 | 19. | 24. | .69 |
| 2.5 | 2.5 | 19.1 | 44. | 21. | 10. | 21. | 24. | .44 |
| 2.5 | .8[i] | 18.3 | 38. | 23. | 14. | 22. | 17. | .33 |
| 2.5 | .8[j] | 18.3 | 41. | 27. | 9.1 | 20. | 21. | .41 |
| 1.25 | .8 | 18.2 | 22. | 39. | 12. | 24. | 4.6 | .18 |
| .62 | .8 | 27.7 | 22. | 40. | 14. | 20. | .87 | .045 |
| .31 | .8 | 24.2 | 37. | 53. | 2. | 7. | .51 | .060 |

[a] Data at 300° C. and 1000 psi. Values are averages of data at various feed gas compositions. The off gas contains approximately 50% CO, 50% $H_2$. Limits shown are average deviations for multiple (usually two) tests. Catalysts contain the indicated weight percentages of rhodium and manganese supported on Davison[TM] Grade 59 Silica Gel.
[b] Dispersion is defined as the fraction of the metal atoms present in the catalyst which are present at the surface of metal crystallites and so are accessible to gas phase molecules. It is measured by determining the number of moles of CO which will chemisorb on a given quantity of catalyst. These analytical procedures are described by S. J. Gregg and K. S. Sing, Adsorption, Surface Area, and Porosity, where CO adsorption is described at pages 263–267 and the dynamic gas chromatographic technique is described at pages 339–343. In this table, the dispersion given is calculated on the assumptions that rhodium chemisorb one molecule of CO per atom of metal exposed but that manganese does not chemisorb CO at all.
[c] Percent carbon efficiency to a particular product is defined as 100 times the number of moles of carbon present in that product divided by the number of moles of CO converted to products other than $CO_2$.
[d] Values given in this table for ethanol and for acetic acid include quantities actually present as ethyl esters and as acetates, respectively.
[e] Units are total pounds of ethanol plus acetic acid plus acetaldehyde produced per cubic foot of catalyst per hour.
[f] Units are total pounds of ethanol plus acetic acid plus acetaldehyde produced per gram of surface Rh (determined as described in footnote [b]) per hour.
[g] The off gas contains approximately 70% CO and 30% $H_2$.
[h] 100 cc of catalyst were charged to the reactor.
[i] 50 cc of catalyst were charged to the reactor.
[j] 20 cc of catalyst were charged to the reactor.

What is claimed is:

1. The process for selectively producing oxygenated hydrocarbon products of two-carbon atoms from a gaseous mixture containing carbon monoxide and hydrogen wherein said gaseous mixture is continuously contacted with a solid catalyst comprising a combination of rhodium and manganese at reaction conditions 250°–350° C., a pressure within the range of about 300–5,000 psig, and a mol ratio of hydrogen to carbon monoxide within the range of about 5:1 to 1:5.

4. Process of claim 1 wherein the space velocity of the gaseous mixture is in excess of about $10^3$ GHSV.

5. Process of claim 4 wherein said space velocity is within the range of about $10^4$ to $10^6$ GHSV.

* * * * *